(12) United States Patent
Breivik (10) Patent No.: US 11,619,737 B2
(45) Date of Patent: Apr. 4, 2023

(54) ULTRASOUND IMAGING SYSTEM AND METHOD FOR GENERATING A VOLUME-RENDERED IMAGE

(71) Applicant: GE Precision Healthcare LLC, Wauwatosa, WI (US)

(72) Inventor: Lars Hofsoy Breivik, Oslo (NO)

(73) Assignee: GE Precision Healthcare, Wauwatosa, WI (US)

( * ) Notice: Subject to any disclaimer, the term of this patent is extended or adjusted under 35 U.S.C. 154(b) by 279 days.

(21) Appl. No.: 16/918,613

(22) Filed: Jul. 1, 2020

(65) Prior Publication Data

US 2022/0000455 A1    Jan. 6, 2022

(51) Int. Cl.
*G01S 15/89*    (2006.01)
*A61B 8/08*    (2006.01)
*A61B 8/00*    (2006.01)

(52) U.S. Cl.
CPC .......... *G01S 15/8988* (2013.01); *A61B 8/461* (2013.01); *A61B 8/483* (2013.01); *A61B 8/488* (2013.01); *A61B 8/5246* (2013.01)

(58) Field of Classification Search
None
See application file for complete search history.

(56) References Cited

U.S. PATENT DOCUMENTS

| | | | | |
|---|---|---|---|---|
| 5,549,111 A | * | 8/1996 | Wright | G01S 7/52047 600/443 |
| 2015/0148679 A1 | * | 5/2015 | Thiele | G01S 15/8979 600/454 |
| 2016/0117857 A1 | * | 4/2016 | State | G06T 19/00 345/420 |
| 2017/0213380 A1 | * | 7/2017 | Samset | A61B 8/0883 |
| 2017/0265845 A1 | * | 9/2017 | Tsushima | G01S 15/8988 |
| 2020/0046324 A1 | * | 2/2020 | Veronesi | G06T 7/40 |

OTHER PUBLICATIONS

Thavendiranathan et al., "Quantitative Assessment of Mitral Regurgitation: How Best to Do It," (Nov. 2012) JACC: Cardiovascular Imaging, vol. 5, Issue 11, pp. 1161-1175. (Year: 2012).*
Da Silva et al., "Interfacial Layers Between Regions of Different Turbulence Intensity," (Oct. 2, 2013) Annu. Rev. Fluid Mech. 2014. 46:567-90. (Year: 2013).*

* cited by examiner

Primary Examiner — Joel Lamprecht
Assistant Examiner — Ashish S Jasani (57) ABSTRACT

An ultrasound imaging system and method includes acquiring volumetric Doppler data, identifying a first subset of the volumetric Doppler data with turbulent characteristics, identifying a second subset of the volumetric Doppler data with non-turbulent characteristics, and generating a volume-rendered image based at least in part on the volumetric Doppler data. Generating the volume-rendered image includes rendering a turbulent flow volume based on the first subset in a first color, rendering a non-turbulent flow volume based on the second subset in two or more colors that are different than the first color. Generating the volume-rendered image includes rendering an outer perimeter of the non-turbulent flow volume with a higher opacity than a central region of the non-turbulent flow volume. The ultrasound imaging system and method includes displaying the volume-rendered image.

20 Claims, 4 Drawing Sheets
(3 of 4 Drawing Sheet(s) Filed in Color)

Prior Art

ULTRASOUND IMAGING SYSTEM AND METHOD FOR GENERATING A VOLUME-RENDERED IMAGE

FIELD OF THE INVENTION

This disclosure relates generally to a method and ultrasound imaging system for generating a volume-rendered image based on volumetric Doppler data.

BACKGROUND OF THE INVENTION

Volume-rendered images are very useful for representing three-dimensional (3D) medical imaging datasets. Volume-rendered images are two-dimensional (2D) representations of a 3D medical imaging dataset. There are currently many different techniques for generating a volume-rendered image. One such technique, ray-casting, includes projecting a number of rays through the 3D medical imaging dataset. Each sample in the 3D medical imaging dataset is mapped to a color and an opacity. Data is accumulated along each of the rays. According to one common technique, the accumulated data along each of the rays is displayed as a pixel in the volume-rendered image.

Ultrasound imaging systems are used to acquire volumetric Doppler data. Volumetric Doppler data is commonly used to view and analyze turbulent flow volumes, such as those associated with a jet from a patient's heart. Unfortunately, when generating a volume-rendered image, it is common for the non-turbulent flow volume to obscure or partially obscure the turbulent flow volumes in the volume-rendered image. This is problematic for clinical situations where it is desired to understand characteristics about the turbulent flow volume.

Therefore, for these and other reasons, an improved system and method for generating volume-rendered images including volumetric Doppler data is desired.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes acquiring volumetric Doppler data with an ultrasound probe, identifying a first subset of the volumetric Doppler data with turbulent characteristics, and identifying a second subset of the volumetric Doppler data with non-turbulent characteristics. The method includes generating a volume-rendered image based at least in part on the volumetric Doppler data. Generating the volume-rendered image includes rendering a turbulent flow volume based on the first subset of the volumetric Doppler data in a first color, rendering a non-turbulent flow volume based on the second subset of the volumetric Doppler data in two or more colors that are different than the first color, wherein an outer perimeter of the non-turbulent flow volume is rendered with a higher opacity than a central region of the non-turbulent flow volume so that the turbulent flow volume is more visible when positioned behind the non-turbulent flow volume compared to if the central region were rendered with the same opacity as the outer perimeter. The method includes displaying the volume-rendered image on a display device.

In another embodiment, an ultrasound imaging system includes a display device, an ultrasound probe, a user interface, and a processor is in electronic communication with the display device and the user interface. The processor is configured to control the ultrasound probe to acquire volumetric Doppler data, identify a first subset of the volumetric Doppler data that exhibits turbulent characteristics, and identify a second subset of the volumetric Doppler data that exhibits non-turbulent characteristics. The processor is configured to generate a volume-rendered image based at least in part on the volumetric Doppler data by: rendering a turbulent flow volume based on the first subset of the volumetric Doppler data in a first color; rendering a non-turbulent flow volume based on the second subset of the volumetric Doppler data in two or more colors that are different than the first color, wherein an outer perimeter of the non-turbulent flow volume is rendered with a higher opacity than a central region of the non-turbulent flow so that the turbulent flow volume is more visible when positioned behind the non-turbulent flow volume compared to if the central region were rendered with the same opacity as the outer perimeter. The processor is configured to display the volume-rendered image on the display device.

Various other features, objects, and advantages of the invention will be made apparent to those skilled in the art from the accompanying drawings and detailed description thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
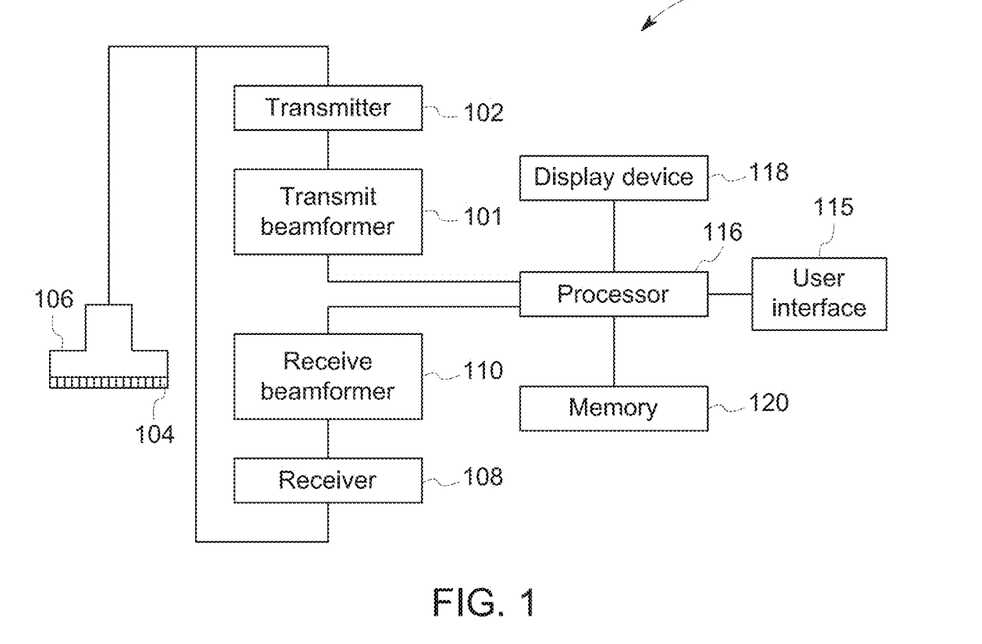
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a body (not shown). The probe 106 may be any type of probe, including a linear probe, a curved array probe, a 1.25D array, a 1.5D array, a 1.75D array, or 2D array probe according to various embodiments. The probe 106 may also be a mechanical probe, such as a mechanical 4D probe or a hybrid probe according to other embodiments. The probe 106 may be used to acquire 4D ultrasound data that contains information about how a volume changes over time. Each of the volumes may include a plurality of 2D images or slices. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit beamforming and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The terms "data" and "ultrasound data" may be used in this disclosure to refer to either one or more datasets acquired with an ultrasound imaging system. A user interface 115 may be used to control operation of the ultrasound imaging system 100. The user interface 115 may be used to control the input of patient data, or to select various modes, operations, and parameters, and the like. The user interface 115 may include a one or more user input devices such as a keyboard, hard keys, a touch pad, a touch screen, a track ball, rotary controls, sliders, soft keys, or any other user input devices. The user interface is in electronic communication with the processor 116.

The ultrasound imaging system 100 also includes a processor 116 to control the transmit beamformer 101, the transmitter 102, the receiver 108 and the receive beamformer 110. The receive beamformer 110 may be either a conventional hardware beamformer or a software beamformer according to various embodiments. If the receive beamformer 110 is a software beamformer, it may comprise one or more of the following components: a graphics processing unit (GPU), a microprocessor, a central processing unit (CPU), a digital signal processor (DSP), or any other type of processor capable of performing logical operations. The beamformer 110 may be configured to perform conventional beamforming techniques as well as techniques such as retrospective transmit beamforming (RTB).

The processor 116 is in electronic communication with the ultrasound probe 106, the receiver 108, the receive beamformer 110, the transmit beamformer 101, and the transmitter 102. The processor 116 may control the probe 106 to acquire ultrasound data. The processor 116 controls which of the elements 104 are active and the shape of a beam emitted from the probe 106. The processor 116 is also in electronic communication with a display device 118, and the processor 116 may process the ultrasound data into images for display on the display device 118. For purposes of this disclosure, the term "electronic communication" may be defined to include both wired and wireless connections. The processor 116 may include a central processing unit (CPU) according to an embodiment. According to other embodiments, the processor 116 may include other electronic components capable of carrying out processing functions, such as a digital signal processor, a field-programmable gate array (FPGA), a graphics processing unit (GPU) or any other type of processor. According to other embodiments, the processor 116 may include multiple electronic components capable of carrying out processing functions. For example, the processor 116 may include two or more electronic components selected from a list of electronic components including: a central processing unit (CPU), a digital signal processor (DSP), a field-programmable gate array (FPGA), and a graphics processing unit (GPU). According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. Real-time frame or volume rates may vary based on the size of the region or volume from which data is acquired and the specific parameters used during the acquisition. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to display as an image. It should be appreciated that other embodiments may use a different arrangement of processors. For embodiments where the receive beamformer 110 is a software beamformer, the processing functions attributed to the processor 116 and the software beamformer hereinabove may be performed by a single processor such as the receive beamformer 110 or the processor 116. Or, the processing functions attributed to the processor 116 and the software beamformer may be allocated in a different manner between any number of separate processing components.

According to an embodiment, the ultrasound imaging system 100 may continuously acquire ultrasound data at a frame-rate of, for example, 10 Hz to 30 Hz. Images generated from the data may be refreshed at a similar frame-rate. Other embodiments may acquire and display data at different rates. For example, some embodiments may acquire ultrasound data at a frame rate of less than 10 Hz or greater than 30 Hz depending on the size of the volume and the intended application. For example, many applications involve acquiring ultrasound data at a frame rate of 50 Hz. A memory 120 is included for storing processed frames of acquired data. In an exemplary embodiment, the memory 120 is of sufficient capacity to store frames of ultrasound data acquired over a period of time at least several seconds in length. The frames of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, color Doppler, M-mode, color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored, and timing information indicating a time at which the data was acquired in memory may be recorded. The modules may include, for example, a scan conversion module to perform scan conversion operations to convert the image frames from beam space coordinates to display space coordinates. A video processor module may be provided that reads the image frames from a memory, such as the memory 120, and displays the image frames in real time while a procedure is being carried out on a patient. A video processor module may store the image frames in an image memory, from which the images are read and displayed.

Figure 2:
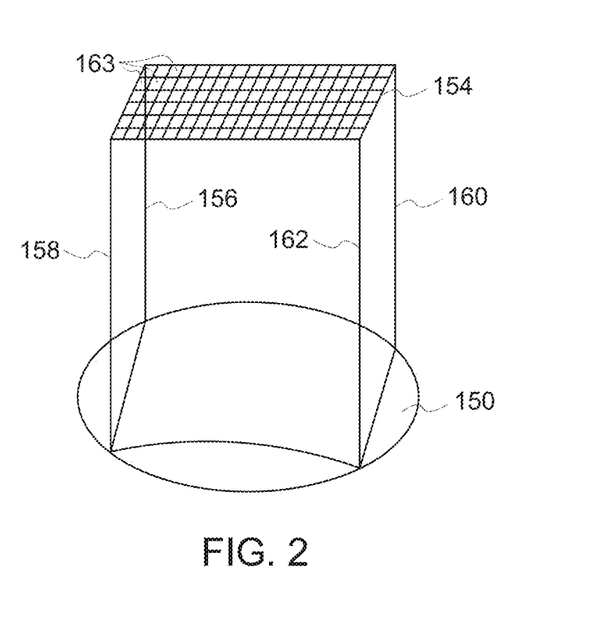
FIG. 2 is a schematic representation of a geometry that may be used to generate a volume-rendered image according to an embodiment.

FIG. 2 is a schematic representation of geometry that may be used to generate a volume-rendering according to an embodiment. FIG. 2 includes a 3D medical imaging dataset 150 and a view plane 154.

Referring to both FIGS. 1 and 2, the processor 116 may generate a volume-rendered image according to a number of different techniques. According to an exemplary embodiment, the processor 116 may generate a volume-rendered image through a ray-casting technique from the view plane 154. The processor 116 may cast a plurality of parallel rays from the view plane 154 to or through the 3D medical imaging dataset 150. FIG. 2 shows a first ray 156, a second ray 158, a third ray 160, and a fourth ray 162 bounding the view plane 154. It should be appreciated that additional rays may be cast in order to assign values to all of the pixels 163 within the view plane 154. The 3D medical imaging dataset 150 may comprise voxel data, where each voxel, or volume-element, is assigned a value or intensity. Additionally, each voxel may be assigned an opacity as well. The value or intensity may be mapped to a color according to some embodiments. The processor 116 may use a "front-to-back" or a "back-to-front" technique for volume composition in order to assign a value to each pixel in the view plane 154 that is intersected by the ray. For example, starting at the front, that is the direction from which the image is viewed, the intensities of all the voxels along the corresponding ray may be summed. Then, optionally, the intensity may be multiplied by an opacity corresponding to the opacities of the voxels along the ray to generate an opacity-weighted value. These opacity-weighted values are then accumulated in a front-to-back or in a back-to-front direction along each of the rays. The process of accumulating values is repeated for each of the pixels 163 in the view plane 154 in order to generate a volume-rendered image. According to an embodiment, the pixel values from the view plane 154 may be displayed as the volume-rendered image. The rendering algorithm used to generate the volume-rendered image may additionally be configured to use an opacity function providing a gradual transition from opacities of zero (completely transparent) to 1.0 (completely opaque). The rendering algorithm may account for the opacities of the voxels along each of the rays when assigning a value to each of the pixels 163 in the view plane 154. For example, voxels with opacities close to 1.0 will block most of the contributions from voxels further along the ray, while voxels with opacities closer to zero will allow most of the contributions from voxels further along the ray. Additionally, when visualizing a surface, a thresholding operation may be performed where the opacities of voxels are reassigned based on the values. According to an exemplary thresholding operation, the opacities of voxels with values above the threshold may be set to 1.0 while voxels with the opacities of voxels with values below the threshold may be set to zero. Other types of thresholding schemes may also be used. An opacity function may be used to assign opacities other than zero and 1.0 to the voxels with values that are close to the threshold in a transition zone. This transition zone may be used to reduce artifacts that may occur when using a simple binary thresholding algorithm. For example, a linear function mapping opacities to values may be used to assign opacities to voxels with values in the transition zone. Other types of functions that progress from zero to 1.0 may also be used. Volume-rendering techniques other than the ones described above may also be used in order to generate a volume-rendering from a 3D medical imaging dataset.

The volume-rendered image may be shaded and illuminated in order to present the user with a better perception of depth of the rendered object represented in the volume-rendered image. This may be performed in several different ways according to various embodiments. For example, a surface of a rendered object in the volume-rendered image may be defined based on the volume-rendering of the 3D medical imaging dataset. According to an exemplary embodiment, a gradient may be calculated at each of the pixels. The processor 116 (shown in FIG. 1) may compute the amount of light at positions corresponding to each of the pixels and apply standard shading methods based on the gradients and specific light directions. The view direction may correspond with the view direction shown in FIG. 2. The processor 116 may also use multiple virtual light sources as inputs when generating the volume-rendered image. For example, when ray casting, the processor 116 may calculate how much light is reflected, scattered, or transmitted from each voxel in a particular view direction along each ray. This may involve summing contributions from multiple virtual light sources. The processor 116 may calculate the contributions from all the voxels in the volume. The processor 116 may calculate composite values from all of the voxels, or interpolated values from neighboring voxels, in order to compute the final value of the displayed pixel on the image. While the aforementioned example described an embodiment where the voxel values are integrated along rays, volume-rendered images may also be calculated according to other techniques such as using the highest value along each ray, using a lowest value along each ray, using an average value along each ray, or using any other volume-rendering technique.

Figure 3:
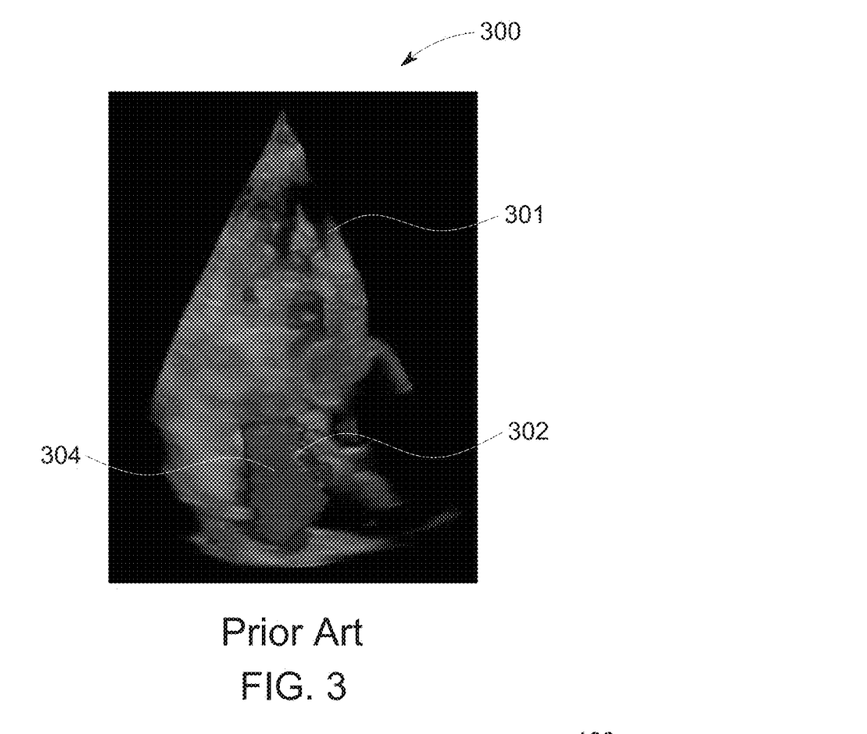
FIG. 3 is a volume-rendered image according to a prior art technique.

FIG. 3 is an example of a volume-rendered image 300 generated according to a prior art technique. The volume-rendered image 300 includes a B-mode volume 301, a turbulent flow volume 302, and a non-turbulent flow volume 304. The B-mode volume 301 is rendered based on B-mode data and both the turbulent flow volume 302 and the non-turbulent flow volume 304 are rendered based on Doppler data. The non-turbulent flow volume 304 is rendered in blue and red in the example shown in FIG. 3. The red represents a portion of the non-turbulent flow volume 304 that is flowing towards the ultrasound probe 106 and the blue represents a portion of the non-turbulent flow volume that is flowing away from the ultrasound probe 106. Clinically, it is oftentimes important to evaluate properties of the turbulent flow volume 302, as the turbulent flow volume 302 oftentimes represents a jet in a patient's heart. However, in the convention technique shown in FIG. 3, the turbulent flow volume 302 is positioned behind a portion of the non-turbulent flow volume 304, which makes it very difficult for a clinician to accurately evaluate characteristics of the turbulent flow volume 302.

Figure 4:
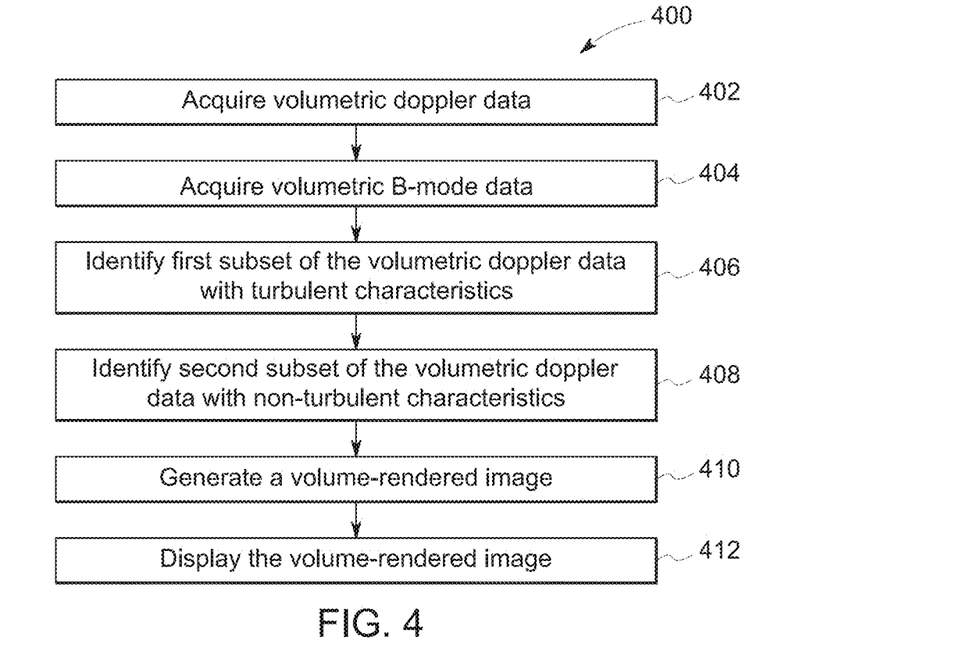
FIG. 4 is a flow chart of a method in accordance with an embodiment.

FIG. 4 is a flow chart of a method 400 in accordance with an embodiment. According to exemplary embodiments, the method 300 may be performed with the ultrasound imaging system 100 shown in FIG. 1. The technical effect of the method 400 is the display of a volume-rendered image including both a turbulent flow volume and a non-turbulent flow volume based on volumetric Doppler data, where an outer perimeter of the non-turbulent flow volume is rendered with a higher opacity than a central region of the non-turbulent flow volume. The technical effect of the method 400 is that the turbulent flow volume is more visible when positioned behind the non-turbulent flow volume compared to if the central region were rendered with the same opacity as the outer perimeter. The method 400 will be described according to an exemplary embodiment where the method 400 is performed with the system 100 shown in FIG. 1.

At step 402, the processor 116 controls the ultrasound probe 106 to acquire volumetric Doppler data. The volumetric Doppler data may be acquired from a volume of interest (VOI). According to an exemplary embodiment, the VOI may be acquired from a heart and it may include at least one jet. The VOI may be acquired from different anatomical area or regions according to various embodiments.

At step 404, the processor 116 controls the ultrasound probe 106 to acquire volumetric B-mode data. The volumetric B-mode data may be acquired from the same VOI as the volumetric Doppler data or the volumetric B-mode data may be acquired from a different VOL According to an exemplary embodiment, the VOI used for the acquisition of the volumetric B-mode data may be a larger volume than the VOI used for the acquisition of the volumetric Doppler data.

Steps 402 and 404 may be performed in either order. According to various embodiments, the processor 116 may control the ultrasound probe 106 to acquire the Doppler data before the B-mode data. Or, the processor 116 may control the ultrasound probe to acquire the Doppler data after the B-mode data. Or, according to an exemplary embodiment, the processor 116 may acquire the volumetric Doppler data and the volumetric B-mode data in an interleaved manner. For example, the processor 116 may control the ultrasound probe 106 to alternate between acquiring one or more frames of the B-mode data and acquiring one or more frames of the Doppler data. According to an exemplary embodiment, the processor 116 may alternate between acquiring one volume of B-mode data and one volume of Doppler data while performing the method 400.

Various characteristics of the volumetric Doppler data are analyzed by the processor 116 in order to determine information of flowing fluids, such as blood, and/or moving tissue within the VOL According to an embodiment, the processor 116 may analyze phases of the signals within the volumetric Doppler data to determine velocities of the flow and/or tissue movement within the VOI used during the acquisition of the volumetric Doppler data. At step 406, the processor 116 identifies a first subset of the volumetric Doppler data with turbulent characteristics. The first subset of the Doppler data with turbulent characteristics may, for instance, exhibit, one or more qualities that are indicative of turbulent flow. At step 408, the processor 116 identifies a second subset of the volumetric Doppler data with non-turbulent characteristics.

According to an example, the processor 116 may use a velocity variance of the volumetric Doppler data to identify the first subset with turbulent characteristics. Doppler data acquired from a region with turbulent flow will typically exhibits a larger velocity variance than Doppler data acquired from a region exhibiting non-turbulent flow. In a non-turbulent flow, the magnitude and the direction (i.e., the velocity) of the flow is more constant since the flow is laminar or relatively close to laminar. Contrastingly, in a turbulent flow, the magnitude and direction (i.e., the velocity) of the flow is likely to change significantly over very short distances due to the turbulent nature of the flow. Therefore, the processor 116 may be configured identify the first subset of the volumetric Doppler data with turbulent characteristics at step 406 by analyzing the velocity variance of the Doppler data. According to an example, the processor 116 may compare the velocity variance of the volumetric Doppler data to a threshold. The processor 116 may, for instance, classify portions of the volumetric Doppler data with a velocity variance greater than the threshold as turbulent and portions of the volumetric Doppler data with a velocity variance equal to or below the threshold as non-turbulent.

Next, at step 410, the processor 116 generates a volume-rendered image. According to an embodiment, the processor 116 may generate the volume-rendered image based on both the volumetric B-mode data and the volumetric Doppler data. According to other embodiments, the volume-rendering may include the volumetric Doppler data without the volumetric B-mode data. An example of how a volume-rendered image may be generated was described with respect to FIG. 2. However, the generation of the volume-rendered image at step 410 will be described in additional detail hereinafter.

According to an exemplary embodiment, the volume-rendered image generated by the processor 116 may be calculated through a technique such as ray-casting. In order to generate the volume-rendered image, it is necessary to perform the ray casting through all the data that will ultimately be included in the displayed volume-rendered image.

Figure 5:
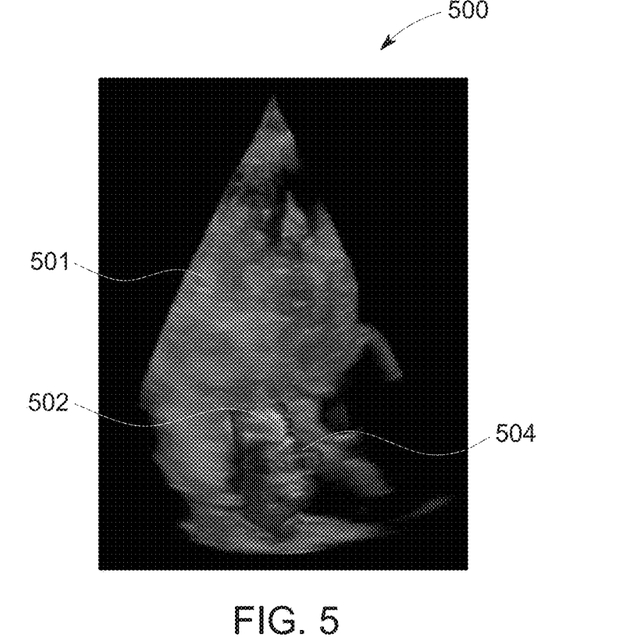
FIG. 5 is a volume-rendered image according to an embodiment.

In the process of generating the volume-rendered image at step 410, the processor 116 renders a turbulent flow volume 502 based on the first subset of the volumetric Doppler data in a first color. FIG. 5 shows a volume-rendered image 500 according to an embodiment. The turbulent flow volume 502 is shown in green in FIG. 5, but any other color may be used to render the turbulent flow volume according to various embodiments.

Figure 6:
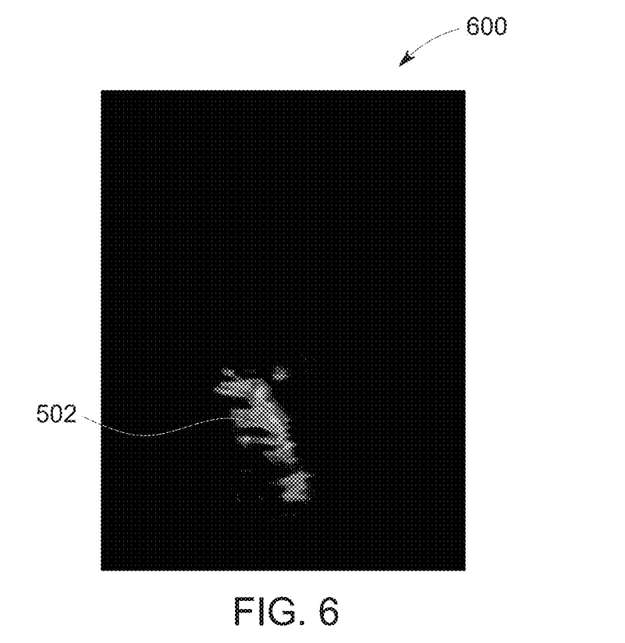
FIG. 6 is a volume-rendered image of a turbulent flow volume according to an embodiment.

FIG. 6 is a volume-rendered image showing just the turbulent flow volume 502. The turbulent flow volume 502 shown in FIG. 6 is the same size and shape as the turbulent flow volume 502 shown in FIG. 5.

Figure 7:
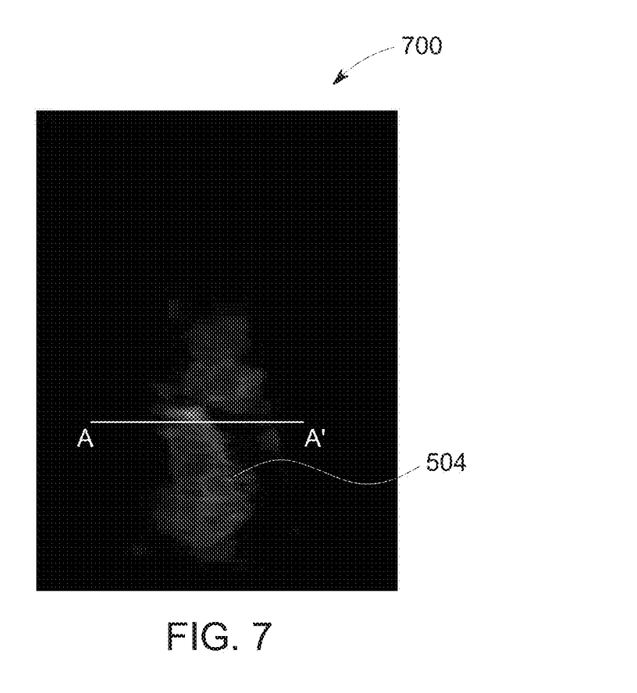
FIG. 7 is a volume-rendered image of a non-turbulent flow volume according to an embodiment.

In the process of generating the volume-rendered image at step 410, the processor 116 also renders a non-turbulent flow volume based on the second subset of the Doppler data. FIG. 7 shows a volume-rendered image of a non-turbulent flow volume 504 according to an embodiment. The non-turbulent flow volume 504 is rendered in two or more colors that are both different than the first color used to identify the turbulent flow volume 502. In the volume-rendered image 500 shown in FIG. 5, the turbulent flow volume 502 has been rendered in green and the non-turbulent flow volume 504 has been rendered in red and blue. One of the two or more colors is used to represent a first flow direction towards the ultrasound probe 106 and a second of the two or more colors is used to represent a second flow direction away from the ultrasound probe 106. According to the example shown in FIG. 6, red is used to represent the first flow direction towards the ultrasound probe 106 and blue is used to represent the second flow direction away from the ultrasound probe 106. While red is used to represent the first flow direction towards the ultrasound probe 106 and blue is used to represent the second flow direction away from the ultrasound probe 106 in the examples shown in FIG. 5 and FIG. 7, other embodiments may use a different color to represent the first flow direction and/or a different color to represent the second flow direction.

According to an embodiment, generating the volume-rendered image at step 410 may also include generating a B-mode volume 501 from the volumetric B-mode data. The volume-rendered image 500 includes the B-mode volume 501 based on the volumetric B-mode data. The volume-rendered image 500 includes the B-mode volume 501, the turbulent flow volume 502 and the non-turbulent flow volume 504. In other embodiments the processor 116 may generate a volume-rendered image that does not include a B-mode volume, such as the B-mode volume 501, generated from the volumetric B-mode data. According to some embodiments, the processor 116 may generate a volume-rendered image that shows just a turbulent flow volume, such as the turbulent flow volume 502, and a non-turbulent flow volume, such as the non-turbulent flow volume 504.

FIG. 3, which depicts the volume-rendered image 300 generated according to a prior art technique, is based on the same volumetric Doppler data and the same volumetric B-mode data as the volume-rendered image 500 shown in FIG. 5. However, in the volume-rendered image 300 shown in FIG. 3, the non-turbulent flow volume 304, which is shown in red and blue colors, obscures or partially obscures the turbulent flow volume 302. According to clinical procedures intended to evaluate properties of the turbulent flow volume 302, the conventional rendering technique shown in FIG. 3 would not be very effective. However, the volume-rendered image 500 is rendered differently at step 410 in the method 400 compared to the conventional rendering technique.

At step 410, the processor 116 renders the second subset of the volumetric Doppler data differently depending upon whether the second subset of the volumetric Doppler data is associated with an outer perimeter or a central region of the non-turbulent flow volume. According to an embodiment, a first portion of the second subset of the volumetric Doppler data may have been acquired from an outer perimeter region of the non-turbulent flow volume and a second portion of the second subset of the volumetric Doppler data may have been acquired from a central region on the non-turbulent flow volume. In order to identify the outer perimeter and the central region, it is therefore necessary for the processor 116 to first identify the first subset of the volumetric Doppler data and the second subset of the volumetric ultrasound data. The non-turbulent flow volume 504 may either be a continuous volume or a discontinuous volume, including two or more discrete volumes. According to an embodiment, the outer perimeter of the of the non-turbulent flow volume may include an outer surface of the non-turbulent flow volume 504 and include a certain depth or thickness towards the central region. The depth of the outer perimeter may be defined by either a number of voxels from the outer surface towards the central region or a thickness defined in a unit of length, such as microns or millimeters. The outer perimeter may be thought of a shell surrounding the central region, where both the outer perimeter (i.e., the "shell") and the central region collectively define the non-turbulent flow volume, such as the non-turbulent flow volume 504.

Figure 8:
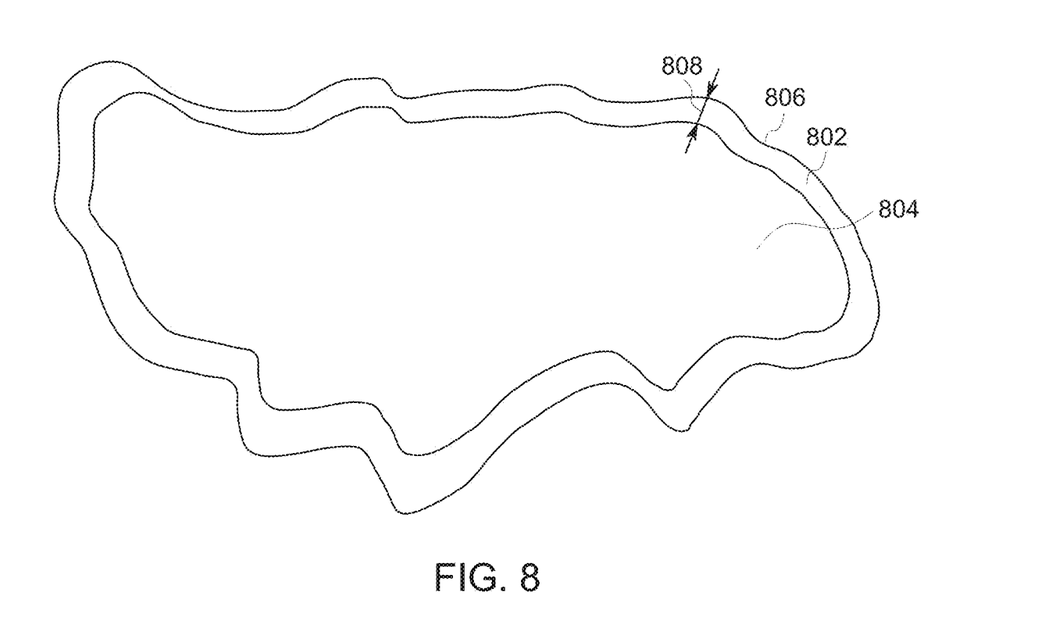
FIG. 8 is a cross-sectional view of the non-turbulent flow volume.

FIG. 8 is a cross-sectional view of the non-turbulent flow volume 504 along the line A-A' shown in FIG. 7. FIG. 8 shows an outer perimeter 802 surrounding a central region 804. The outer perimeter 802 is defined to include a thickness 808 from the outer surface 806. As described above, the thickness 808 may be defined to be a certain number of voxels from the outer surface 806 towards the central region 804, or the thickness may be defined to be a specific thickness in a unit of length from the outer surface 806 towards the central region 804. According to some embodiments, the thickness 808 of the outer perimeter 802 may be user selectable or controllable through the user interface 115. According to an embodiment, the thickness of the outer perimeter 802 may be between 1 mm and 5 mm. According to an exemplary embodiment, the thickness of the outer perimeter 802 may be between 2 mm and 4 mm. It should be appreciated that other embodiments may use a thickness of the outer perimeter 802 that is either thicker than 5 mm or thinner than 1 mm. According to an example, the thickness of the outer perimeter 802 may be automatically calculated by the processor 116 to be a percentage of a dimension of the VOI.

During the process of generating the volume-rendered image at step 410, the processor 116 renders the outer perimeter 802 with a different opacity than the central region 804. At step 410, the processor 116 is configured to render the outer perimeter 802 of the non-turbulent flow volume 504 with a higher opacity than the central portion 802. According to an embodiment, both the volumetric Doppler data and the volumetric B-mode data may both be organized as voxel data. The value associated with each voxel, or volume element, represents the Doppler data or the B-mode data acquired from a spatial location associated with that particular voxel. While generating the volume-rendered image at step 410, the processor 116 assigns each voxel a color and an opacity and then performs a rendering operation such as ray-casting. When rendering the non-turbulent flow volume 504, the processor 116 assigns a greater opacity to voxels associated with the outer perimeter 802 than to voxels associated with the central region 804. According to an embodiment, the processor 116 may assign an opacity to voxels in the central region 804 that is a fixed amount lower than the opacity assigned to voxels in the outer perimeter 802. According to another embodiment, the opacity assigned to voxels in the central region 804 may be zero, so that the central region of the non-turbulent volume 504 is completely translucent. According to another embodiment, the opacity of the central region may be user-selectable. For example, the processor 116 may be configured to adjust the opacity of the central region between zero (i.e., completely translucent) and an opacity that is just less than the opacity of the outer perimeter 802 in response to an input from the user interface 115. According to another embodiment, the processor 116 may be configured to automatically adjust the opacity of the central region 804 to smoothly transition back-and-forth between an opacity of zero and a higher opacity that is less than the opacity of the outer perimeter 802. For example, the processor 116 may control the opacity of the central region 804 to smoothly increase from zero to a maximum opacity for the central region and back from the maximum opacity to zero. The processor 116 may cause the opacity of the central region to smoothly oscillate between the maximum opacity for the central region and a minimum opacity for the central region, such as zero, until the user enter a command through the user interface 115 to stop automatically adjusting the opacity.

By rendering the central portion 804 with a lower opacity than the outer perimeter 802, the non-turbulent flow volume 504 is rendered with a much lower overall opacity in the volume-rendered image 500. The non-turbulent flow volume 504 is rendered with higher opacity values in the outer perimeter in order to give the user a clear indication of the overall size and shape of the non-turbulent flow volume 504, but the central portion 804 is rendered with a lower opacity to reduce the overall opacity of the non-turbulent flow volume 504. By rendering the central region 802 with a lower opacity, it is still possible for the user to clearly see the turbulent flow volume 502 even when the turbulent flow volume 502 is positioned behind some or all of the non-turbulent flow volume 504.

For example, FIG. 6 shows a volume-rendered image 600 of the turbulent flow volume 502 without either the B-mode volume 501 or the non-turbulent flow volume 504. The volume-rendered image 500, shown in FIG. 5, is a volume-rendered image generated according to the method described in the method 400. As such, the non-turbulent flow volume 504 is rendered so that the outer perimeter 802 has a higher opacity than the central region 804. In the volume-rendered image 500 shown in FIG. 5, it is easy to see that the turbulent flow volume 502 has the same size and shape as the turbulent flow volume 502 shown in FIG. 6. In contrast, in FIG. 3, which represent a prior art rendering technique of the same data represented in FIG. 5, the non-turbulent flow volume 304 obscures much of the turbulent flow volume 302. Depending on the shapes of the non-turbulent flow volume and the turbulent flow volume, the prior art technique, such as that shown in FIG. 5, may make it difficult or impossible to accurately analyze the turbulent flow volume 302. FIG. 5 shows an example where central region 804 of the non-turbulent flow region 504 is rendered with the same opacity as the outer perimeter 802 and FIG. 5 shows an example where the central region 804 is rendered with an opacity that is less than the outer perimeter 802. FIGS. 5 and 3 are both rendered from the same data and show the respective volumes from the same view angle. Comparing FIG. 5 to FIG. 3, it is apparent that rendering the outer perimeter 802 with a higher opacity than the central region 804 results in a turbulent flow volume that is much more visible than when the central region 804 is rendered with the same opacity as the outer perimeter 802, as shown in FIG. 3.

According to an embodiment, to further increase the visibility of the turbulent flow volume 502, the turbulent flow volume 502 may be rendered with an opacity that is higher than the outer perimeter 802 of the non-turbulent flow volume 502. According to an embodiment, the turbulent flow volume 502 may be rendered with an opacity that is higher than the central region 804 of the non-turbulent flow volume 502.

Next, at step 412, the processor 116 displays the volume-rendered image 500 on the display device 116. According to an embodiment, the processor 116 may be configured to generate and display the volume-rendered image in real-time. For example, the volume-rendered image may be a live, or real-time image that is updated as additional volumetric Doppler data and additional Volumetric B-mode data are acquired. According to an embodiment, the processor may iteratively perform steps 402, 404, 406, 408, 410, and 412 while performing an ultrasound scan of a patient. The processor 116 may, for instance, display an updated frame of the volume-rendered image as additional volumetric Doppler data and additional Volumetric B-mode data are acquired. According to an example, the processor 116 is configured to update the volume-rendered image each time data for an additional VOI has been acquired. According to an embodiment, the frame rate of the live volume-rendered image may be based on the volume rate of acquisition of the VOI for the volumetric Doppler data and/or the volume rate of acquisition of VOI for the volumetric B-mode data. According to some embodiments, the volume rate of acquisition for the volumetric Doppler data may be different than the volume rate of acquisition for the volumetric B-mode data. This may be useful, for instance, for embodiments where the VOI used for the volumetric Doppler data is considerably smaller than the VOI used for the volumetric B-mode data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A method of ultrasound imaging comprising:
acquiring volumetric Doppler data with an ultrasound probe;
identifying a first subset of the volumetric Doppler data with turbulent blood flow characteristics;
identifying a second subset of the volumetric Doppler data with non-turbulent blood flow characteristics;
generating a volume-rendered image based at least in part on the volumetric Doppler data, wherein generating the volume-rendered image comprises:
rendering a turbulent flow volume based on the first subset of the volumetric Doppler data in a first color;
rendering a non-turbulent flow volume based on the second subset of the volumetric Doppler data in two or more colors that are different than the first color, wherein an outer perimeter of the non-turbulent flow volume is rendered with a higher opacity than a central region of the non-turbulent flow volume, wherein the turbulent flow volume is rendered with a higher opacity than the central region of the non-turbulent flow volume when the turbulent flow volume is positioned behind some or all of the non-turbulent flow volume with respect to a view direction of the volume-rendered image and
displaying the volume-rendered image on a display device.

2. The method of claim 1, wherein a first of the two or more colors is used to represent a first flow direction towards an ultrasound probe and a second of the two or more colors is used to represent a second flow direction away from the ultrasound probe.

3. The method of claim 2, wherein the first of the two or more colors is red and the second of the two or more colors is blue.

4. The method of claim 3, wherein the first color is green.

5. The method of claim 1, wherein the turbulent flow volume is rendered with a higher opacity than the central region of the non-turbulent flow volume.

6. The method of claim 5, wherein the turbulent flow volume is rendered with a higher opacity than the outer perimeter of the non-turbulent flow volume.

7. The method of claim 1, wherein the turbulent flow volume represents turbulent flow from a jet in a heart.

8. The method of claim 1, wherein the central region of the non-turbulent flow volume is rendered with a user selectable opacity.

9. The method of claim 1, wherein the central region of the non-turbulent flow volume is rendered as transparent.

10. The method of claim 1, wherein the volume-rendered image is a live volume-rendered image.

11. The method of claim 1, wherein the non-turbulent flow volume includes two or more discrete non-turbulent flow volumes.

12. The method of claim 1, further comprising:
acquiring volumetric B-mode data with the ultrasound probe;
and wherein said generating the volume-rendered image further comprises rendering a B-mode volume based on the volumetric B-mode data.

13. An ultrasound imaging system comprising:
a display device;
an ultrasound probe;
a user interface; and
a processor in electronic communication with the display device and the user interface, wherein the processor is configured to:
control the ultrasound probe to acquire volumetric Doppler data;
identify a first subset of the volumetric Doppler data that exhibits turbulent blood flow characteristics;
identify a second subset of the volumetric Doppler data that exhibits non-turbulent blood flow characteristics;
generate a volume-rendered image based at least in part on the volumetric Doppler data by:
rendering a turbulent flow volume based on the first subset of the volumetric Doppler data in a first color;
rendering a non-turbulent flow volume based on the second subset of the volumetric Doppler data in two or more colors that are different than the first color, wherein an outer perimeter of the non-turbulent flow volume is rendered with a higher opacity than a central region of the non-turbulent flow, wherein the turbulent flow volume is rendered with a higher opacity than the central region of the non-turbulent flow volume when the turbulent flow volume is positioned behind some or all of the non-turbulent flow volume with respect to a view direction of the volume-rendered image; and
display the volume-rendered image on the display device.

14. The ultrasound imaging system of claim 13, wherein the processor is configured to identify the first subset of the volumetric Doppler data based on a velocity variance of the volumetric Doppler data.

15. The ultrasound imaging system of claim 13, wherein the processor is configured to apply an illumination and a shading to the volume rendering of the volumetric Doppler data based on the position of a virtual light source.

16. The ultrasound imaging system of claim, 13, wherein a first of the two or more colors is red and a second of the two or more colors is blue, and wherein the red is used to represent a first flow direction towards the ultrasound probe and the blue is used to represent a second flow direction away from the ultrasound probe.

17. The ultrasound imaging system of claim 13, wherein the turbulent flow volume represents a jet in a heart.

18. The ultrasound imaging system of claim 13, wherein the processor is configured to render the central region as transparent.

19. The ultrasound imaging system of claim 13, wherein the processor is further configured to:
control the ultrasound probe to acquire volumetric B-mode data;
and wherein the processor is further configured to generate the volume-rendered image by rendering a B-mode volume based on the volumetric B-mode data.

20. The ultrasound imaging system of claim 19, wherein the processor is configured to control the ultrasound probe to acquire the volumetric Doppler data and the volumetric B-mode data in an interleaved manner.

* * * * *